(12) United States Patent
Yeh

(10) Patent No.: US 12,186,094 B2
(45) Date of Patent: Jan. 7, 2025

(54) WEARABLE DEVICE

(71) Applicant: Advanced Semiconductor Engineering, Inc., Kaohsiung (TW)

(72) Inventor: Chang-Lin Yeh, Kaohsiung (TW)

(73) Assignee: ADVANCED SEMICONDUCTOR ENGINEERING, INC., Kaohsiung (TW)

( * ) Notice: Subject to any disclaimer, the term of this patent is extended or adjusted under 35 U.S.C. 154(b) by 642 days.

(21) Appl. No.: 17/396,605

(22) Filed: Aug. 6, 2021

(65) Prior Publication Data

US 2023/0042984 A1 Feb. 9, 2023

(51) Int. Cl.
*A61B 5/00* (2006.01)
*H05K 5/00* (2006.01)
*H05K 5/06* (2006.01)

(52) U.S. Cl.
CPC ......... *A61B 5/6801* (2013.01); *H05K 5/0086* (2013.01); *H05K 5/065* (2013.01); *A61B 2562/18* (2013.01)

(58) Field of Classification Search
CPC ..... A61B 5/6801; H05K 5/0086; H05K 5/065
USPC ......................................................... 600/300
See application file for complete search history.

(56) References Cited

U.S. PATENT DOCUMENTS

2012/0095352 A1\* 4/2012 Tran ..................... A61B 5/6803
600/490
2020/0296825 A1 9/2020 Ozdoganlar et al.

\* cited by examiner

*Primary Examiner* — Nadia A Mahmood
(74) *Attorney, Agent, or Firm* — FOLEY & LARDNER LLP

(57) ABSTRACT

A wearable device is provided. The wearable device includes an electronic component and an encapsulant. The encapsulant includes a low-penetrability region encapsulating the electronic component and a high-penetrability region physically separated from the electronic component.

17 Claims, 13 Drawing Sheets

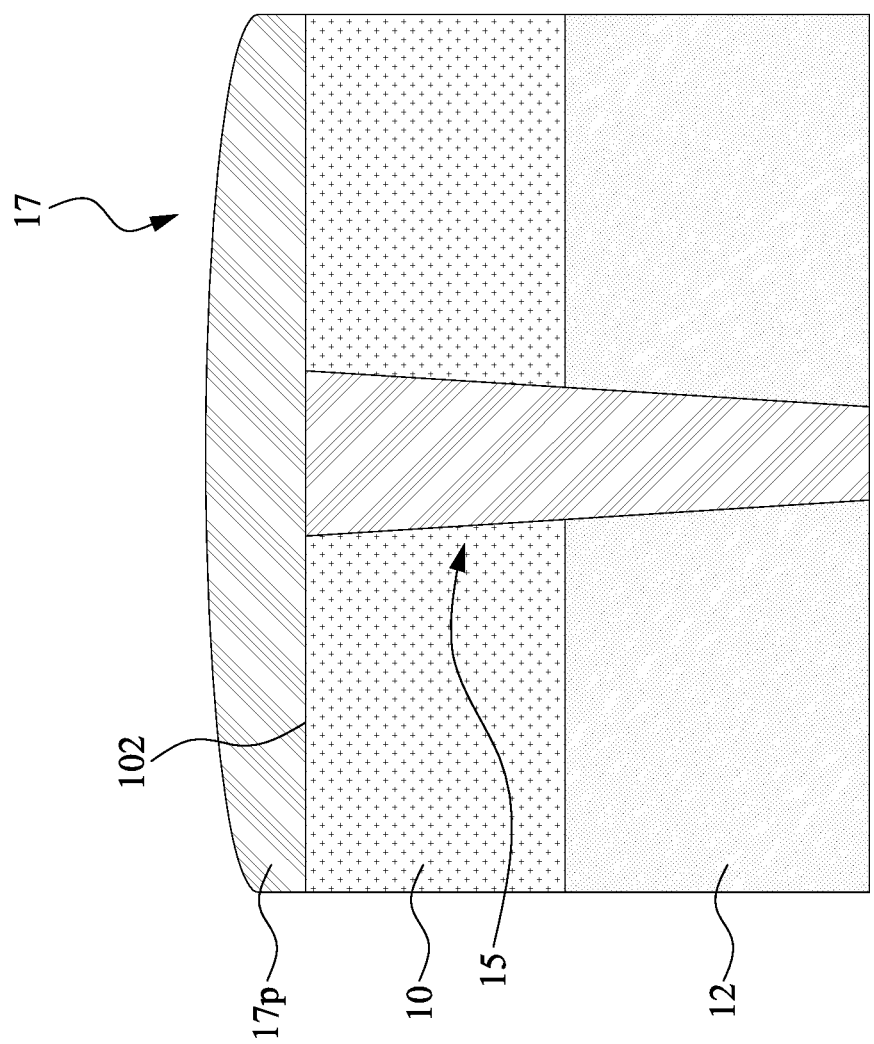

WEARABLE DEVICE

BACKGROUND

1. Field of the Disclosure

The present disclosure relates to a wearable device.

2. Description of the Related Art

Wearable devices may include some encapsulating materials to protect the components therein. However, these encapsulating materials may not be breathable or permeable for sweat. As such, wearers may feel uncomfortable when the wearable devices are in contact with their skin.

SUMMARY

In some embodiments, a wearable device includes an electronic component and an encapsulant. The encapsulant includes a low-penetrability region encapsulating the electronic component and a high-penetrability region physically separated from the electronic component.

In some embodiments, a wearable device includes a transferring region and a wiring region. The transferring region is configured to transfer matter from a body to the external environment. The wiring region includes a wiring element physically separated from the transferring region.

BRIEF DESCRIPTION OF THE DRAWINGS

Aspects of some embodiments of the present disclosure are readily understood from the following detailed description when read with the accompanying figures. It is noted that various structures may not be drawn to scale, and dimensions of the various structures may be arbitrarily increased or reduced for clarity of discussion.

FIG. 4A illustrates an enlarged view of a dotted box B1 as shown in FIG. 1 according to some embodiments of the present disclosure.

DETAILED DESCRIPTION

Figure 1:
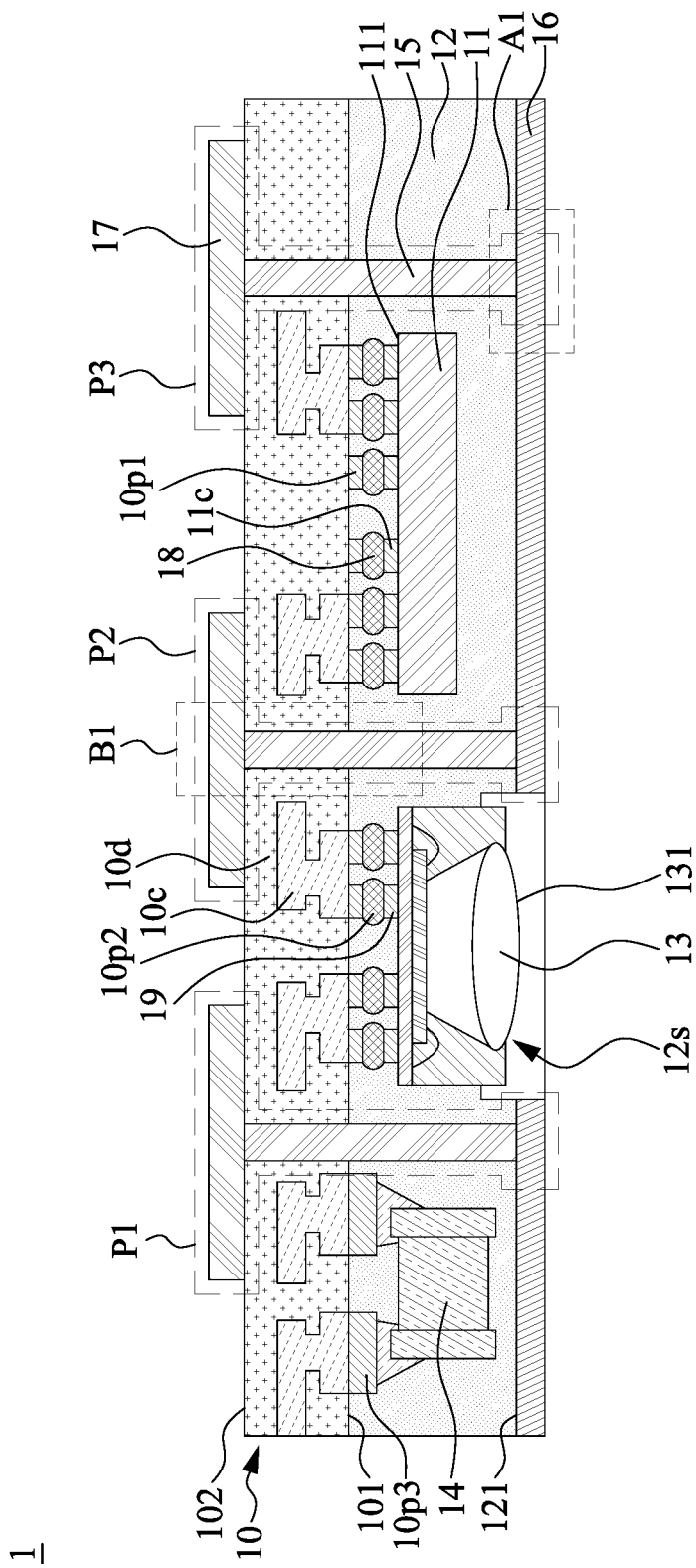
FIG. 1 illustrates a cross-sectional view of a wearable device according to some embodiments of the present disclosure.

Common reference numerals are used throughout the drawings and the detailed description to indicate the same or similar components. Embodiments of the present disclosure will be readily understood from the following detailed description taken in conjunction with the accompanying drawings.

The following disclosure provides many different embodiments, or examples, for implementing different features of the provided subject matter. Specific examples of components and arrangements are described below to explain certain aspects of the present disclosure. These are, of course, merely examples and are not intended to be limiting. For example, the formation of a first feature over or on a second feature in the description that follows may include embodiments in which the first and second features are formed or disposed in direct contact, and may also include embodiments in which additional features may be formed or disposed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

FIG. 1 illustrates a cross-sectional view of a wearable device 1 according to some embodiments of the present disclosure. The wearable device 1 may include a carrier 10, an electronic component 11, an encapsulant 12, a sensing element 13, an electronic component 14, a hole 15, a region 16, a region 17, a connection element 18, and a connection element 19. The wearable device 1 may be adaptive to a body, e.g., of a wearer. The body may include a body part, i.e., skin, finger, wrist, elbow, arm, chest, neck, ear, thigh, knee, leg, foot, or others.

The carrier 10 may be bendable. For example, the outline of the carrier 10 may be pliable, twistable, and/or stretchable. The carrier 10 may include a bendable material, a flexible material, or a soft material. The carrier 10 may include, but is not limited to, silicone or rubber.

The carrier 10 may have a surface 101 and a surface 102 opposite to the surface 101. The carrier 10 may include a conductive pad 10p1, a conductive pad 10p2, and a conductive pad 10p3 disposed on the surface 101. The carrier 10 may include a substrate. The carrier 10 (or a substrate) may include a redistribution layer (RDL) structure including a dielectric layer 10d and a wiring layer 10c disposed in the dielectric layer 10d. The wiring layer 10c may include one or more wiring element. The dielectric layer 10d may cover the wiring layer 10c. The wiring layer 10c may be electrically connected to one of the conductive pads 10p1, 10p2, or 10p3. The wiring layer 10c may include one or more metals such as copper (Cu), gold (Au), aluminum (A), titanium (Ti) or the like. The conductive pads 10p1, 10p2, and 10p3 may each include one or more metals such as copper (Cu), gold (Au), aluminum (A), titanium (Ti) or the like. The dielectric layer 10d may include, but is not limited to, an organic material such as a molding compound, an epoxy-based material or other suitable organic materials.

The electronic component 11 may be disposed on the surface 101 of the carrier 10. The electronic component 11 may have an active surface 111 facing the carrier 10. The electronic component 11 may include a conductive pad 11c on the active surface 111. The conductive pad 11c of the electronic component 11 may be electrically connected with the conductive pad 10c1 of the carrier 10 through the connection element 18. The electronic component 11 may include an integrated circuit, a controller, a micro-controller unit (MCU), a memory, etc. The electronic component 11 may include a semiconductor die.

The sensing element 13 may be disposed on the surface 101 of the carrier 10. The sensing element 13 may have a sensing surface 131 facing away from the carrier 10. The sensing element 13 may include a conductive pad 13c. The conductive pad 13c of the sensing element 13 may be electrically connected with the conductive pad 10c1 of the carrier 10 through the connection element 19. The sensing element 13 may be configured to detect a signal of a wearer (or a wearer's body). The sensing element 13 may be configured to detect a biosignal. The biosignal may include: a pulse travel time (PTT), an electroencephalogram (EEG), electrocardiogram (ECG), electromyogram (EMG), heart rate variability (HRV), oxygen saturation (unit $SpO_2$). The sensing element 13 may include an emitter configured to emit a first signal and a receiver configured to receive second signal associated with first signal. The first signal and the second signal may each include radiation. The first signal and the second signal may each include a visible light, a non-visible light, an infrared light, microwaves, or the like. The sensing element 13 may be electrically connected to the electronic component 11 through the wiring layer 10c of the carrier 10. The sensing element 13 may be configured to transmit the biosignal to the electronic component 11. The electronic component 11 may be configured to process the biosignal. The electronic component 11 may be configured to convert the biosignal into digital data for subsequent processing. The electronic component 11 may be configured to store the processed data. The electronic component 11 may be configured to transmit the processed data or the biosignal data to an external device via attached wiring, or wirelessly.

The electronic component 14 may be disposed on the surface 101 of the carrier 10. The electronic component 14 may be electrically connected to the carrier 10 through the conductive pad 10p3. The electronic component 14 may include a passive device such as a capacitor, an inductor, or a resistor. The electronic component 14 may include an active device such as a transistor, or a switch.

The encapsulant 12 may be disposed on the surface 101 of the carrier 10. The encapsulant 12 may have a surface facing away from the carrier 10. The encapsulant 12 may encapsulate the electronic component 11 and/or the electronic component 14. The encapsulant 12 may define a space 12s. The space 12s may be configured to accommodate the sensing element 13. The sensing surface 131 of the sensing element 13 may be exposed by the encapsulant 12. As such, the encapsulant 12 may not hinder the sensing of the sensing element 13. In an alternative embodiment, the sensing element 13 may be configured to sense a signal other than a light, and the encapsulant 12 may encapsulate the sensing element 13. In another alternative embodiment, the encapsulant 12 may include a transparent material and may encapsulate the sensing element 13 without hindering the sensing thereof.

The encapsulant 12 may include an epoxy resin with or without fillers, a molding compound (e.g., an epoxy molding compound or other molding compound), a polyimide, a phenolic compound or material, a material with a silicone dispersed therein, or a combination thereof.

The hole 15 (e.g., a region) may penetrate the carrier 10. The hole 15 may be spaced apart from the wiring layer 10c. The wiring layer 10c and a portion of the dielectric layer 10d may define a circuit region (e.g., a wiring structure or a wiring region) of the carrier 10. The hole 15 may extend to the circuit region of the carrier 10. The hole 15 may extend to the wiring structure configured to electrically connect to the electronic component 11. In an alternative embodiment, the hole 15 (e.g., a region) may penetrate the wiring element of the wiring layer 10c. The hole 15 may penetrate the encapsulant 12. The hole 15 may have a taper shape. The hole 15 may have a pillar shape. The hole 15 may have a cylinder shape. The hole 15 may be filled with a porous material. The porous material may include plastic balls or silica. In some embodiments, the hole 15 may be hollow.

The region 16 may be configured to collect a fluid from a wearer. The region 16 may be a fluid collecting region. The region 16 may be disposed on the surface 121 of the encapsulant 12. The fluid collecting region 16 may fully or partially cover the surface 121 of the encapsulant 12. The fluid collecting region 16 may be connected to the hole 15. The fluid collecting region 16 may at least partially overlap the electronic component 11 in a direction substantially perpendicular to an active surface of the electronic component. The fluid collecting region 16 may be configured to collect matter (or fluid) from the body of a wearer.

Figure 2A:
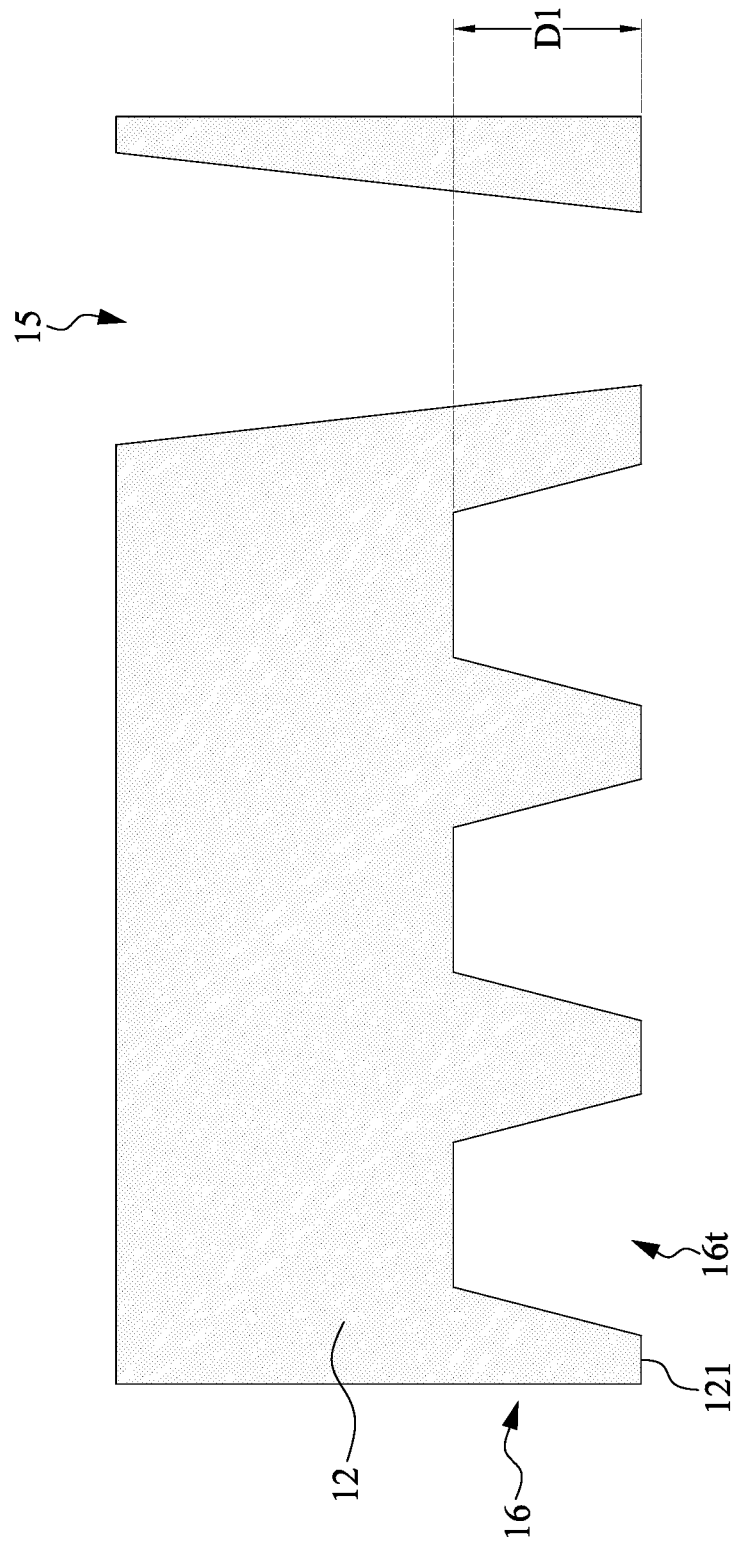
FIG. 2A illustrates an enlarged view of a dotted box A1 as shown in FIG. 1 according to some embodiments of the present disclosure.

FIG. 2A illustrates an enlarged view of a dotted box A1 as shown in FIG. 1 according to some embodiments of the present disclosure. As shown in FIG. 2A, the hole 15 may be hollow. The encapsulant 12 may include at least one trench 16t disposed at the fluid collecting region 16. The trenches 16t may extend from the surface 121 of the encapsulant 12 into the encapsulant 12 with a depth D1. The trenches 16t may not expose the electronic component 11. The trenches 16t may increase the contacting area between the wearable device and the body of a wearer. As such, the fluid collecting region 16 may be configured to more efficiently collect matter (or fluid) from the body of a wearer.

Figure 2B:
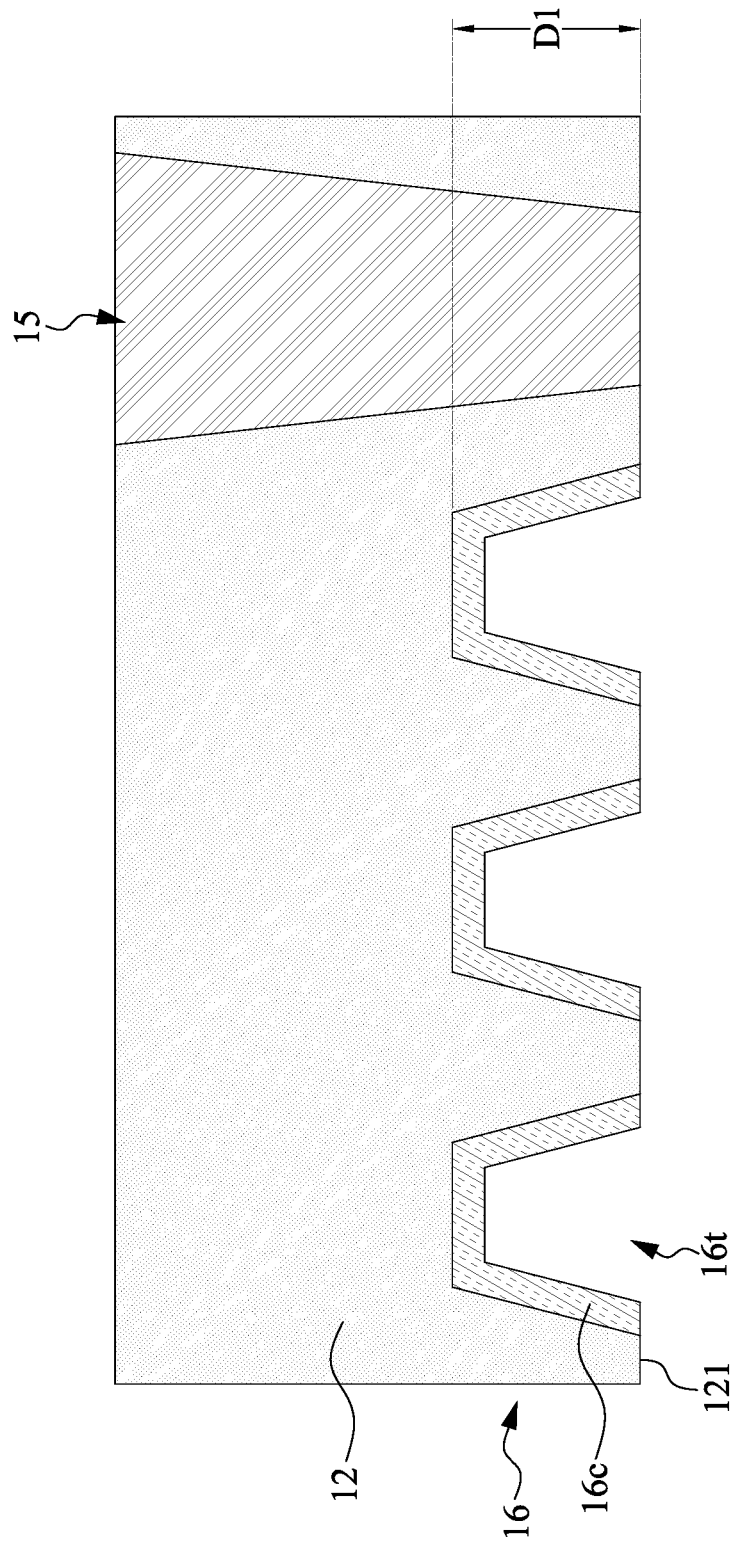
FIG. 2B illustrates another enlarged view of a dotted box A1 as shown in FIG. 1 according to some embodiments of the present disclosure.

FIG. 2B illustrates another enlarged view of a dotted box A1 as shown in FIG. 1 according to some embodiments of the present disclosure. The structure of FIG. 2B is similar to the structure of FIG. 2A, and the differences therebetween are described below.

A coating 16c may be disposed along the bottom and the sidewall of the trenches 16t. The coating 16c may include a hydrophilic material. The coating 16c may be beneficial to the collecting capability of the fluid collecting region 16.

Figure 2C:
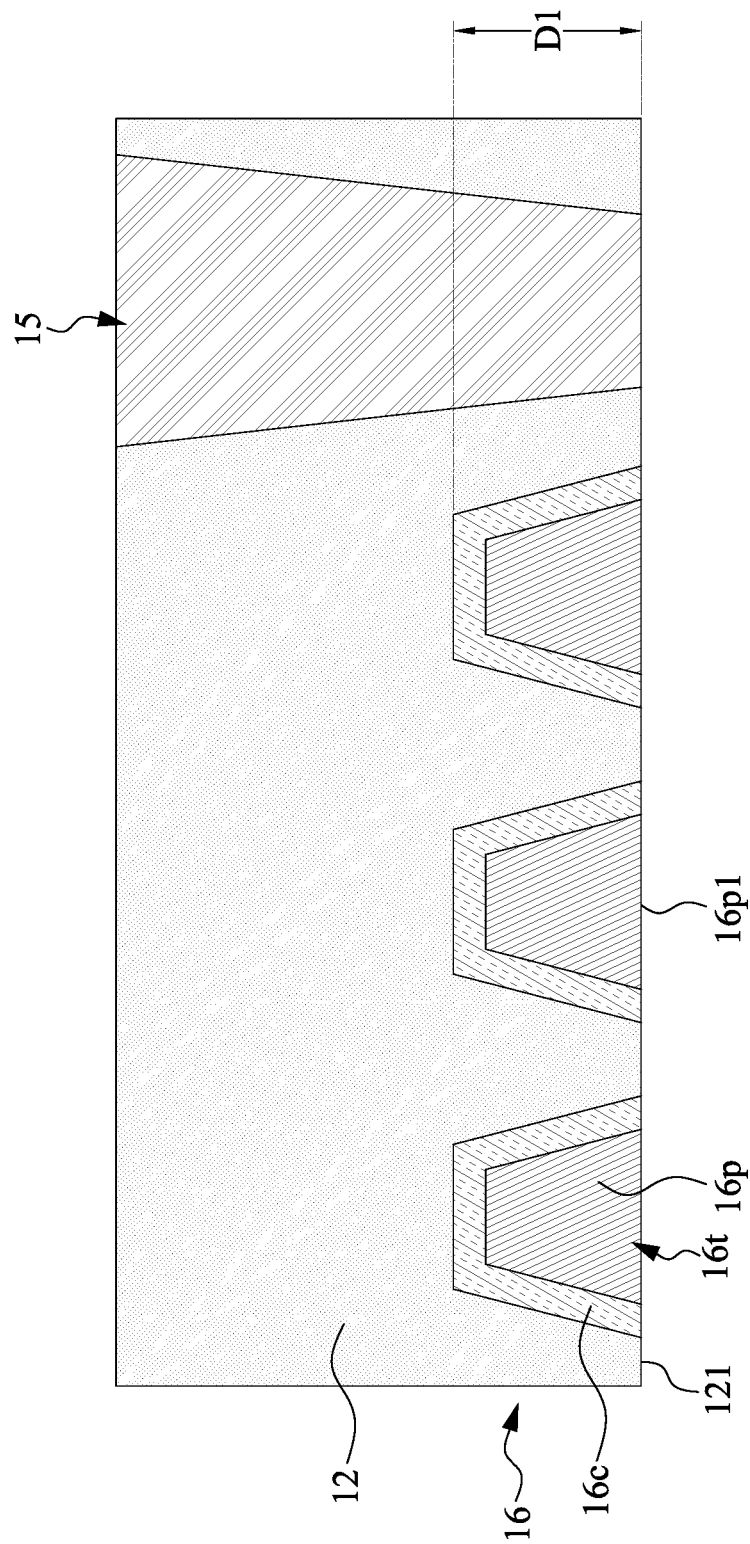
FIG. 2C illustrates another enlarged view of a dotted box A1 as shown in FIG. 1 according to some embodiments of the present disclosure.

FIG. 2C illustrates another enlarged view of a dotted box A1 as shown in FIG. 1 according to some embodiments of the present disclosure. The structure of FIG. 2C is similar to the structure of FIG. 2B, and the differences therebetween are described below.

A layer 16p may be disposed in the trenches 16t. The layer 16p may be disposed on the coating 16c. The layer 16p may have a surface 16p1 exposed by the encapsulant 12. The surface 16p1 of the layer 16p and the surface 121 of the encapsulant 12 may be substantially coplanar. In some embodiments, the surface 16p1 of the layer 16p may protrude from the surface 121 of the encapsulant 12. In some embodiments, the surface 16p1 of the layer 16p may be recessed from the surface 121 of the encapsulant 12. The layer 16p may include a hydrophilic material that is beneficial to the collecting capability of the fluid collecting region 16. The layer 16p may include, for example, but is not limited to, a porous material.

Figure 3B:
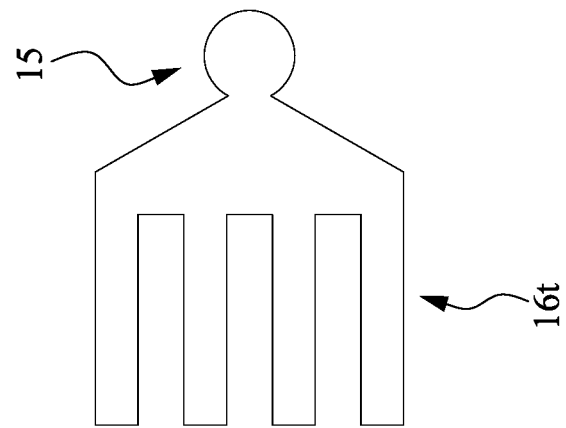
FIG. 3B illustrates another bottom view of a dotted box A1 as shown in FIG. 1 according to some embodiments of the present disclosure.
Figure 3A:
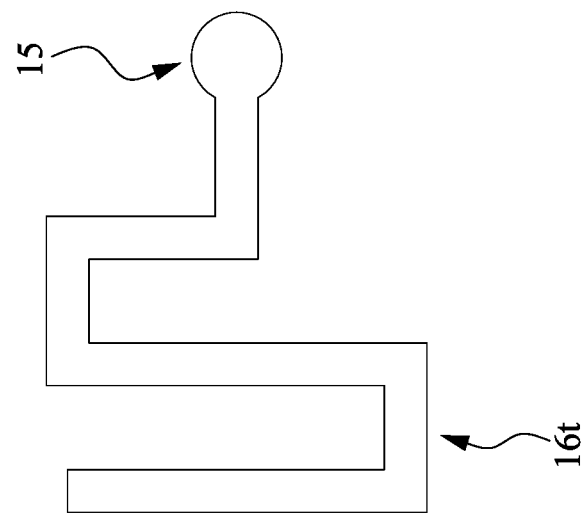
FIG. 3A illustrates a bottom view of a dotted box A1 as shown in FIG. 1 according to some embodiments of the present disclosure.

FIG. 3A illustrates a bottom view of a dotted box A1 as shown in FIG. 1 according to some embodiments of the present disclosure. As shown in FIG. 3A, the bottom view of the hole 15 may have a circular shape. In some embodiments, the hole 15 may have a rectangular, triangular, an oval shape, or the like. The trenches 16t may be connected to the hole 15. The trenches 16t may have a meander shape.

FIG. 3B illustrates another bottom view of a dotted box A1 as shown in FIG. 1 according to some embodiments of the present disclosure. As shown in FIG. 3A, the trenches 16t may be connected to the hole 15. The trenches 16t may have a comb shape.

Referring again to FIG. 1, the region 17 may be disposed on the surface 102 of the carrier 10. The region 17 may be configured to drain fluid to external environment. The region 17 may be a fluid draining region 17. The fluid draining region 17 and the fluid collecting region 16 may be disposed at opposite sides of the encapsulant 12. The fluid draining region 17 may be connected to the hole 15. The hole 15 may be configured to connect the fluid draining region 17 with the fluid collecting region 16. In other words, the region 15 may be configured to connect the region 16 with the region 17 and configured to transfer matter from the region 16 to the region 17. The fluid draining region 17 may be configured to drain matter (or fluid) from the hole 15.

FIG. 4A illustrates an enlarged view of a dotted box B1 as shown in FIG. 1 according to some embodiments of the present disclosure. A layer 17p may be disposed at the fluid draining region 17. The layer 17p may be disposed on the surface 102 of the carrier 10. The layer 17p may be connected to the hole 15. The layer 17p may include a water-loving material that helps drain the matter (or fluid) from the hole 15. The layer 17p may include a porous material.

Figure 4B:
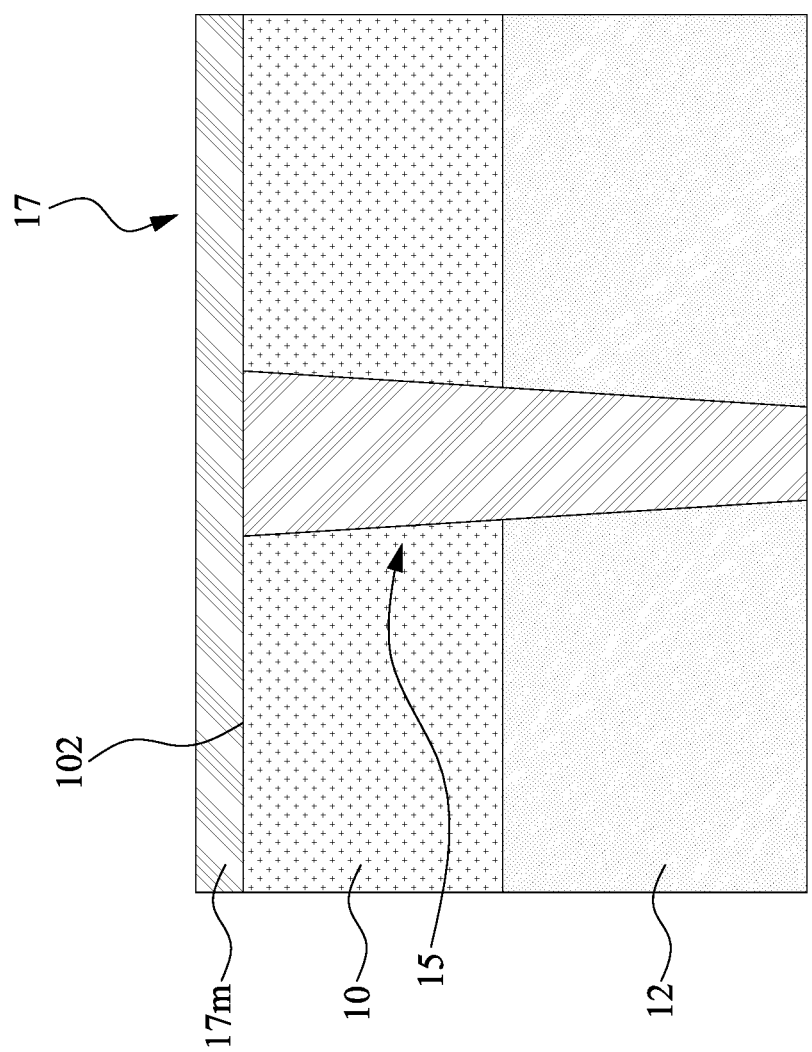
FIG. 4B illustrates another enlarged view of a dotted box B1 as shown in FIG. 1 according to some embodiments of the present disclosure.

FIG. 4B illustrates another enlarged view of a dotted box B1 as shown in FIG. 1 according to some embodiments of the present disclosure. A mesh 17m may be disposed at the fluid draining region 17. The mesh 17m may be disposed on the surface 102 of the carrier 10. The mesh 17m may be connected to the hole 15. The layer 17p may include a breathable material that helps drain the matter (or fluid) from the hole 15.

Figure 4C:
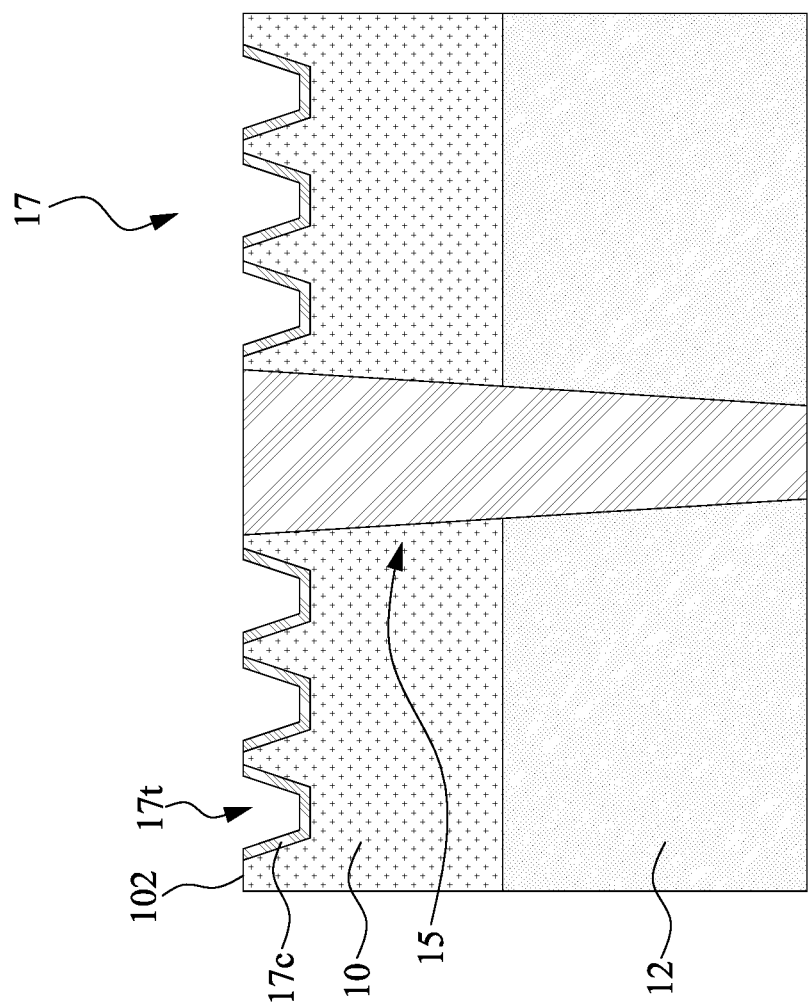
FIG. 4C illustrates another enlarged view of a dotted box B1 as shown in FIG. 1 according to some embodiments of the present disclosure.

FIG. 4C illustrates another enlarged view of a dotted box B1 as shown in FIG. 1 according to some embodiments of the present disclosure. The carrier 10 may include at least one of the trenches 17t disposed at the fluid draining region 17. The trenches 17t may extend from the surface 102 of the carrier 10 into the carrier 10. The trenches 17t may increase the area of the fluid draining region 17 that is exposed to the external environment (or the air). As such, the fluid draining region 17 may be configured to more efficiently drain matter (or fluid) from the hole 15.

A coating 17c may be disposed along the bottom and the sidewall of the trenches 17t. The coating 17c may include a hydrophilic material. The coating 17c may be beneficial to the collecting capability of the fluid collecting region 17.

Referring again to FIG. 1, the wearable device 1 may include a high-penetrability region P1 (or a transferring region) between the electronic component 14 and the sensing element 13, a high-penetrability region P2 between the sensing element 13 and the electronic component 11, and a high-penetrability region P3 adjacent to the electronic component 11. The high-penetrability region P1, P2, or P3 may each include a portion of the dielectric layer 10d of the carrier 10, a portion of the encapsulant 12, and the hole 15. In other words, a portion of the dielectric layer 10d of the carrier 10, a portion of the encapsulant 12, and the hole 15 may be disposed at each of the high-penetrability regions P1, P2 and P3. The wiring layer 10c of the carrier 10 may be free from passing through the high-penetrability region P1, P2, or P3. The circuit region of the carrier 10 may be physically separated from the high-penetrability region P1, P2, or P3 (i.e., the transferring region). Furthermore, the high-penetrability region P1, P2, or P3 may include a portion of the fluid collecting region 16 and a portion of the fluid draining region 17. In other words, a portion of the fluid collecting region 16 and a portion of the fluid draining region 17 may be disposed at each of the high-penetrability regions P1, P2 and P3. Furthermore, the high-penetrability region P1, P2, or P3 may include the trenches 16t at the fluid collecting region 16. In addition, the high-penetrability region P1, P2, or P3 may include the mesh 16m or the layer 16p at the fluid collecting region 16. The high-penetrability region P1, P2, or P3 may include the trenches 17t at the fluid draining region 17. In addition, the high-penetrability region P1, P2, or P3 may include the mesh 17m or the layer 17p at the fluid draining region 17.

The wearable device 1 may include a low-penetrability region defined by the imaginary boundaries of the high-penetrability regions P1, P2, and P3 (shown as dashed lines in FIG. 1). The high-penetrability region P1, P2, or P3 may be configured to allow matter (or fluid) to pass through more efficiently than the low-penetrability region does. The matter may include liquid or gas. The matter may include the sweat of a body. The matter may penetrate through a region with a high penetrability (e.g., the high-penetrability region P1, P2, or P3) with less resistance than a region with a low penetrability (e.g., the low-penetrability region). The low-penetrability region may include an unbreathable region. The low-penetrability region may include a gas-impermeable region. The low-penetrability region may include a fluid-impermeable region.

The low-penetrability region may include the wiring layer 10c and a portion of the dielectric layer 10d of the carrier 10 and a portion of the encapsulant 12. In other words, the wiring layer 10c and a portion of the dielectric layer 10d of the carrier 10 and a portion of the encapsulant 12 may be disposed at the low-penetrability region. The low-penetrability region may encapsulate the electronic component 11 and/or the electronic component 14. However, the high-penetrability region P1, P2, or P3 may be disconnected from the electronic component 11 and/or the electronic component 14. A sensing region may be disposed adjacent to the low-penetrability region. The sensing element 13 may be disposed at the sensing region. The low-penetrability region may surround the sensing region (or the sensing element 13). A penetrability of the sensing region may be lower than a penetrability of the high-penetrability regions P1, P2, and P3 (or the transferring region) and higher than a penetrability of the circuit region of the carrier 10. The sensing region may be electrically connected to the circuit region of the carrier 10.

In some embodiments, the low-penetrability region may include a portion of the fluid collecting region 16. In other words, a portion of the fluid collecting region 16 may be disposed at the low-penetrability region. In some embodiments, the low-penetrability region may include the electronic component 11, the sensing element 13, or the electronic component 14. In other words, the electronic component 11, the sensing element 13, or the electronic component 14 may be disposed at the low-penetrability region.

Figure 5:
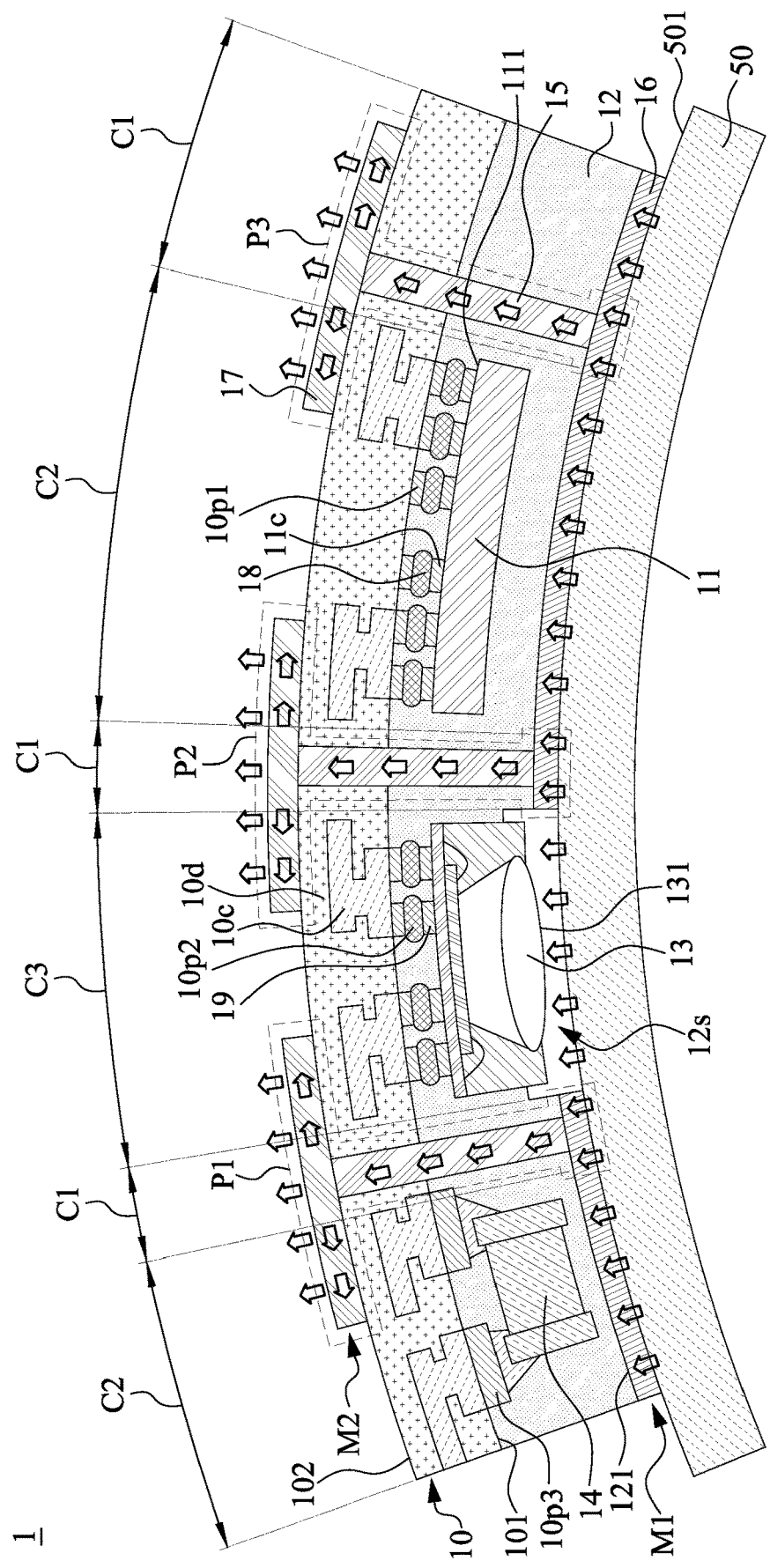
FIG. 5 illustrates a cross-sectional view of a wearable device being adapted to a body according to some embodiments of the present disclosure.

FIG. 5 illustrates a cross-sectional view of a wearable device (e.g., the wearable device 1) being adapted to a body 50 according to some embodiments of the present disclosure. As shown in FIG. 5, the wearable device 1 may be bent when the wearable device 1 is adapted to the body 50. The body 50 may have a curved surface 501 facing the wearable device 1. The body 50 may belong to a wearer. The body 50 may include a body part, i.e., skin, finger, wrist, elbow, arm, chest, neck, ear, thigh, knee, leg, foot, or others.

The fluid collecting region 16 may be closer to a wearer (i.e., the body 50) when the wearable device 1 is worn by the wearer. The fluid collecting region 16 may be closer to a wearer (i.e., the body 50) compared with the electronic component 11 when the wearable device 1 is worn by the wearer. The fluid draining region 17 may be far away from the wearer (i.e., the body 50) compared with the electronic component 11 when the wearable device 1 is worn by the wearer. The fluid collecting region 16 and the fluid draining region 17 are at different sides of the wearable device 1. The fluid collecting region 16 is closer to the body 50 compared with the fluid draining region 17.

The fluid collecting region 16 may be adhesive such that the wearable device 1 may be adhered to the body 50 (or the curved surface 501) through the fluid collecting region 16. In an alternative embodiment, the wearable device 1 may include one or more adhesive elements (e.g., in the fluid collecting region 16) configured for the adhesion between the wearable device 1 and the body 50. The fluid collecting region 16 may be in contact with the curved surface 501 of the body 50. The fluid collecting region 16 may be configured to collect matter (or fluid) of the body 50 as indicated with a plurality of arrows M1. The fluid collecting region 16 may be connected to the high-penetrability regions P1, P2, and P3, which are physically separated from the electronic component 11, the sensing element 13, or the electronic component 14. The matter may be transferred to the high-penetrability regions P1, P2, and P3. The matter may then be transferred within the high-penetrability regions P1, P2, and P3 in a direction from the fluid collecting region 16 to the fluid draining region 17 through the hole 15 as indicated by a plurality of arrows M2. The matter may then be released into the external environment. The matter may not accumulate on the curved surface 501. Instead, the matter would be transferred by the high-penetrability regions P1, P2, and P3, such that the wearer would have a comfortable experience when wearing the wearable device 1.

The wearable device 1 may include a high-bendability region C1 substantially aligned with the high-penetrability region P1, P2, or P3 and a low-bendability region C2 substantially aligned with the low-penetrability region. The high-bendability region C1 may be bent to a greater extent than the low-bendability region C2 when the wearable device 1 is adapted to the body 50. In other words, the high-bendability region C1 may be easier to be bent than the low-bendability region C2. The high-bendability region C1 may be bent to conform to the curved surface 501, while the low-bendability region C2 may be rigid enough to retain the shape. The curvature of the low-bendability region C2 may be lower than the curvature of the high-bendability region C1 when the wearable device 1 is worn.

The high-bendability region C1 may be free from the electronic component 11. The electronic component 11 may be disposed at the low-bendability region C2. The wiring layer 10c of the carrier may be disposed at the high-bendability region C1 and the low bendability region C2. The sensing element 13 may be disposed at a region C3 having a bendability between a bendability of the high-bendability region C1 and a bendability of the low-bendability region C2. In some embodiments, the fluid collecting region 16 may have a bendability higher than a bendability of the circuit region of the carrier 10.

Figure 6A:
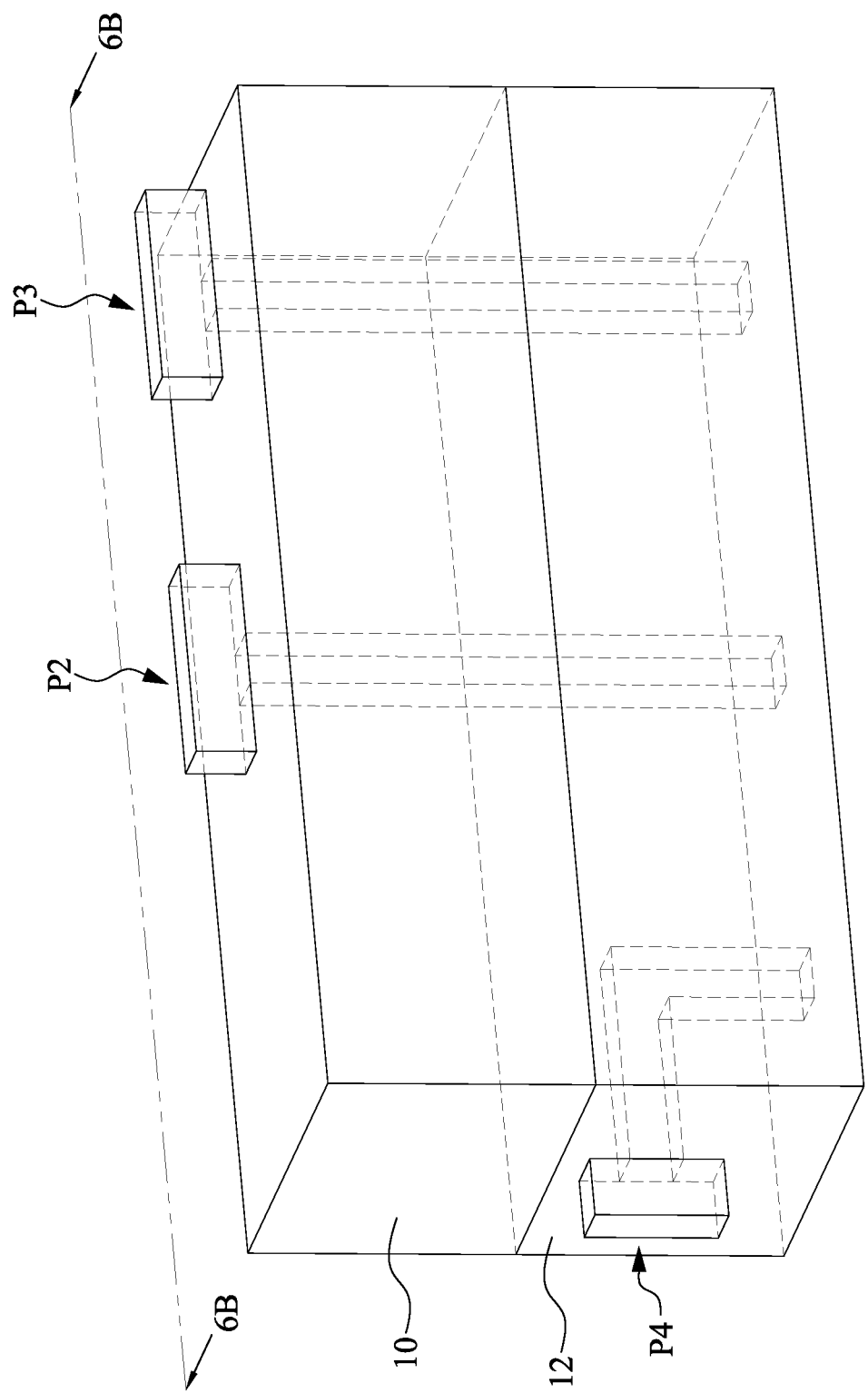
FIG. 6A illustrates a 3D view of a wearable device being adapted to a body according to some embodiments of the present disclosure.
Figure 6B:
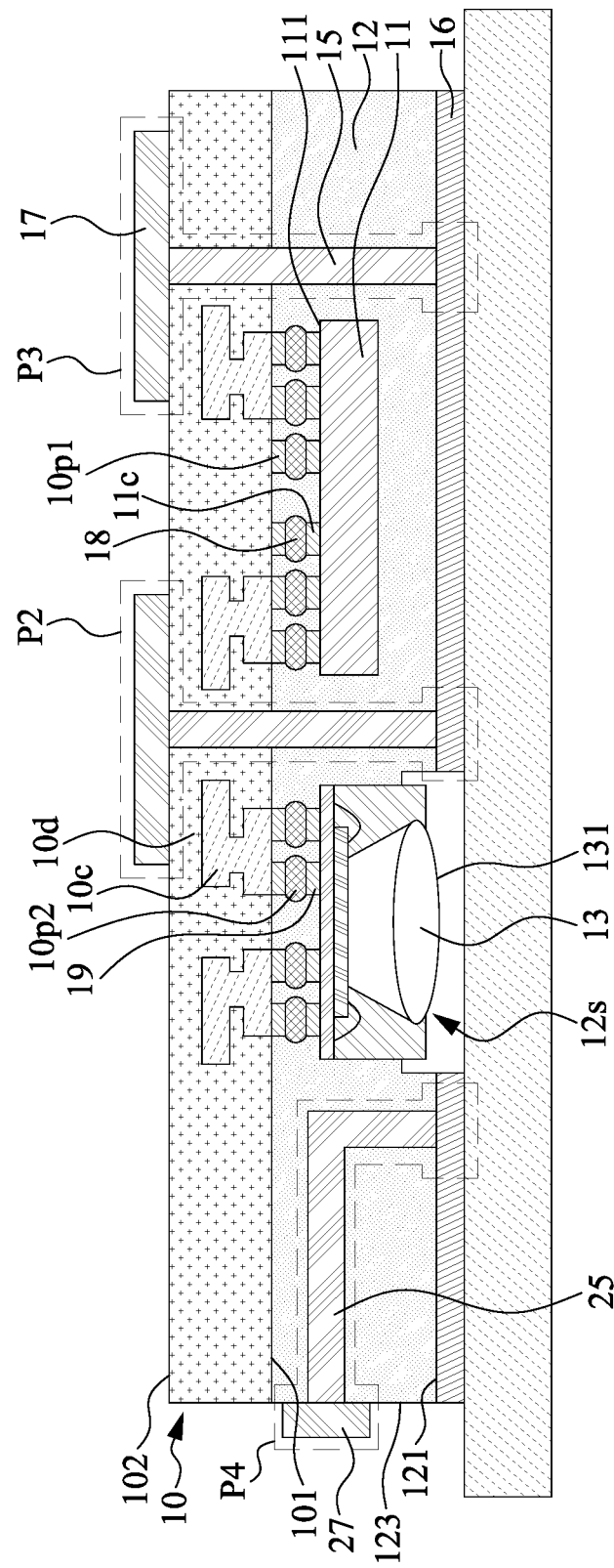
FIG. 6B illustrates a cross-sectional view along the 6B-6B line in FIG. 6A.

FIG. 6A illustrates a 3D view of a wearable device 2 being adapted to a body 50 according to some embodiments of the present disclosure. FIG. 6B illustrates a cross-sectional view along the 6B-6B line in FIG. 6A. The wearable device 2 of FIG. 6A and FIG. 6B is similar to the wearable device 1 of FIG. 1, and the differences therebetween are described below.

The wearable device 2 may include a hole 25 extending from a lateral surface 123 of the encapsulant 12. The wearable device 2 may include a fluid draining region 27 disposed on the lateral surface 123 of the encapsulant 12. The fluid draining region 27 may cover an end of the hole 25. The fluid draining region 27 may be connected to the hole 25. The hole 25 may configured to connect the fluid collecting region 16 with the fluid draining region 27. The fluid draining region 27 and the fluid collecting region 16 may be disposed at two adjacent sides of the encapsulant 12.

Figure 7A:
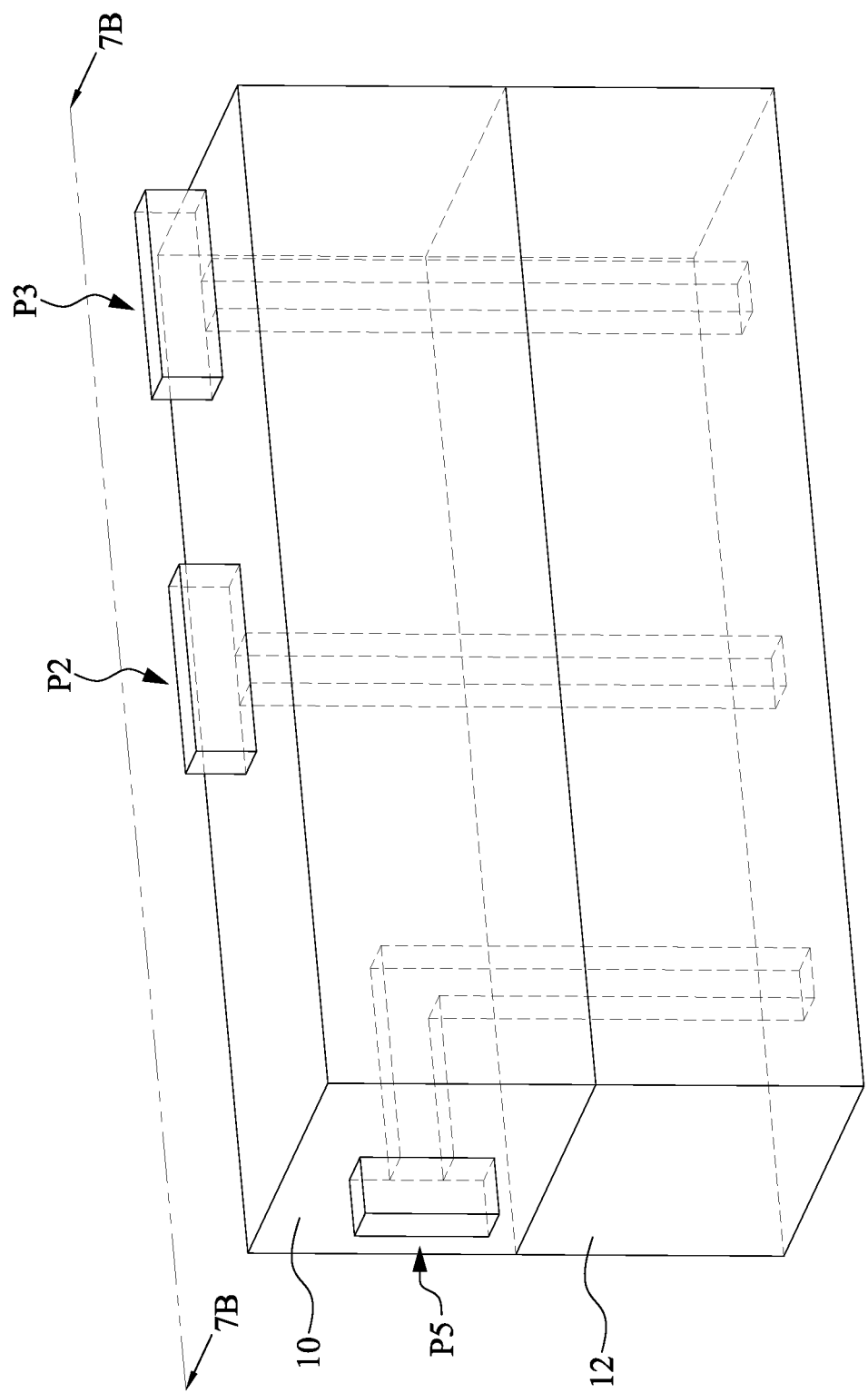
FIG. 7A illustrates a 3D view of a wearable device being adapted to a body according to some embodiments of the present disclosure.
Figure 7B:
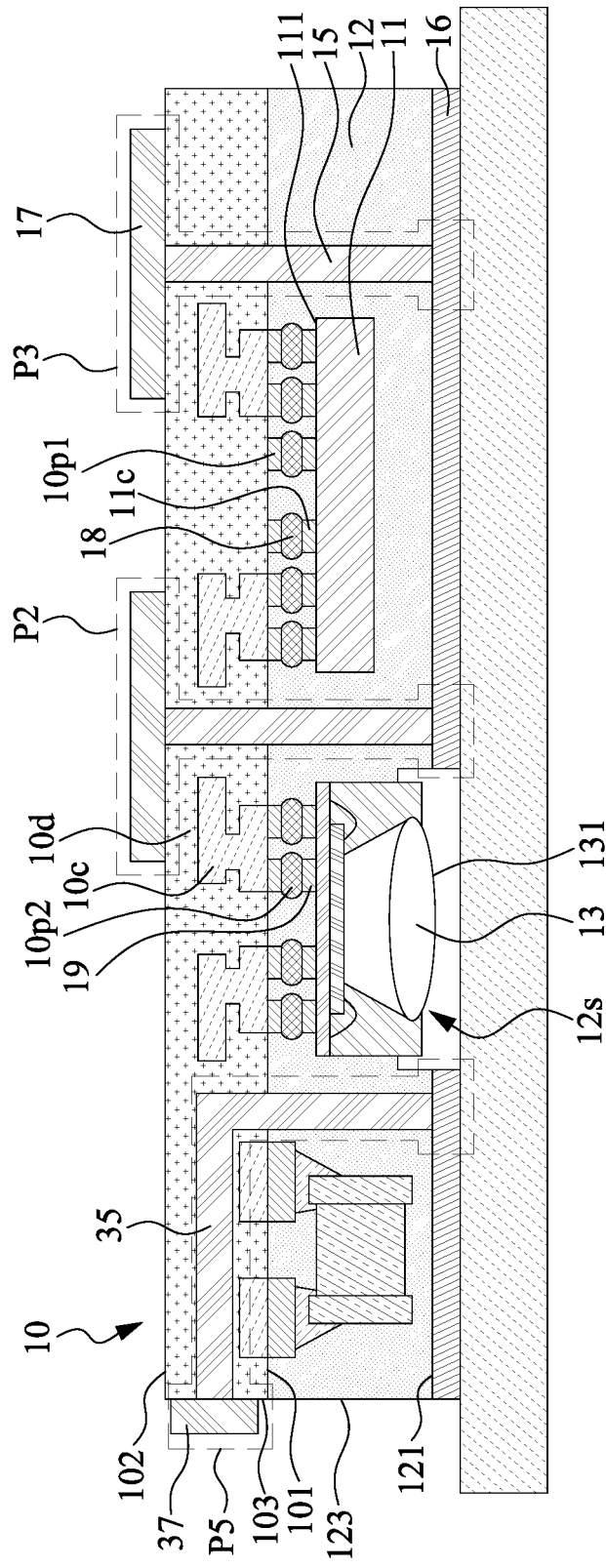
FIG. 7B illustrates a cross-sectional view along the 7B-7B line in FIG. 7A.

FIG. 7A illustrates a 3D view of a wearable device 3 being adapted to a body 50 according to some embodiments of the present disclosure. FIG. 7B illustrates a cross-sectional view along the 7B-7B line in FIG. 7A. The wearable device 3 of FIG. 7A and FIG. 7B is similar to the wearable device 1 of FIG. 1, and the differences therebetween are described below.

The wearable device 3 may include a hole 35 extending from a lateral surface 103 of the carrier 10. The wearable device 3 may include a fluid draining region 37 disposed on the lateral surface 103 of the carrier 10. The fluid draining region 37 may cover an end of the hole 35. The fluid draining region 37 may be connected to the hole 35. The hole 35 may configured to connect the fluid collecting region 16 with the fluid draining region 37.

Spatial descriptions, such as "above," "below," "up," "left," "right," "down," "top," "bottom," "vertical," "horizontal," "side," "higher," "lower," "upper," "over," "under," and so forth, are indicated with respect to the orientation shown in the figures unless otherwise specified. It should be understood that the spatial descriptions used herein are for purposes of illustration only, and that practical implementations of the structures described herein can be spatially arranged in any orientation or manner, provided that the merits of embodiments of this disclosure are not deviated from by such an arrangement.

As used herein, the terms "approximately," "substantially," "substantial" and "about" are used to describe and account for small variations. When used in conjunction with an event or circumstance, the terms can refer to instances in which the event or circumstance occurs precisely as well as instances in which the event or circumstance occurs to a close approximation. For example, when used in conjunction with a numerical value, the terms can refer to a range of variation less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, two numerical values can be deemed to be "substantially" the same or equal if a difference between the values is less than or equal to ±10% of an average of the values, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%.

Two surfaces can be deemed to be coplanar or substantially coplanar if a displacement between the two surfaces is no greater than 5 µm, no greater than 2 µm, no greater than 1 µm, or no greater than 0.5 µm.

As used herein, the singular terms "a," "an," and "the" may include plural referents unless the context clearly dictates otherwise.

As used herein, the terms "conductive," "electrically conductive" and "electrical conductivity" refer to an ability to transport an electric current. Electrically conductive materials typically indicate those materials that exhibit little or no opposition to the flow of an electric current. One measure of electrical conductivity is Siemens per meter (S/m). Typically, an electrically conductive material is one having a conductivity greater than approximately $10^4$ S/m, such as at least $10^5$ S/m or at least $10^6$ S/m. The electrical conductivity of a material can sometimes vary with temperature. Unless otherwise specified, the electrical conductivity of a material is measured at room temperature.

Additionally, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified.

While the present disclosure has been described and illustrated with reference to specific embodiments thereof, these descriptions and illustrations are not limiting. It should be understood by those skilled in the art that various changes may be made and equivalents may be substituted without departing from the true spirit and scope of the present disclosure as defined by the appended claims. The illustrations may not be necessarily drawn to scale. There may be distinctions between the artistic renditions in the present disclosure and the actual apparatus due to manufacturing processes and tolerances. There may be other embodiments of the present disclosure which are not specifically illustrated. The specification and drawings are to be regarded as illustrative rather than restrictive. Modifications may be made to adapt a particular situation, material, composition of matter, method, or process to the objective, spirit and scope of the present disclosure. All such modifications are intended to be within the scope of the claims appended hereto. While the methods disclosed herein have been described with reference to particular operations performed in a particular order, it will be understood that these operations may be combined, sub-divided, or re-ordered to form an equivalent method without departing from the teachings of the present disclosure. Accordingly, unless specifically indicated herein, the order and grouping of the operations are not limitations of the present disclosure.

What is claimed is:

1. A wearable device, comprising:
    an electronic component;
    an encapsulant including a low-penetrability region encapsulating the electronic component and a high-penetrability region physically separated from the electronic component; and
    a hole disposed at the high-penetrability region and penetrating the encapsulant.

2. The wearable device of claim 1, wherein the high-penetrability region is configured to allow a fluid to pass through more efficiently than the low-penetrability region does.

3. The wearable device of claim 1, wherein the hole further extends to a wiring structure configured to electrically connect to the electronic component.

4. The wearable device of claim 1, further comprising:
    a sensing region disposed adjacent to the low-penetrability region; and
    a sensing element disposed at the sensing region, wherein the sensing element is configured to detect a signal of a wearer and electrically connect to the electronic component.

5. The wearable device of claim 4, further comprising a wiring layer free from passing through the high-penetrability region and electrically connecting the sensing element with the electronic component.

6. A wearable device, comprising:
    an electronic component;
    an encapsulant including a low-penetrability region encapsulating the electronic component and a high-penetrability region physically separated from the electronic component;
    a high-bendability region substantially aligned with the high-penetrability region; and
    a low-bendability region substantially aligned with the low-penetrability region.

7. The wearable device of claim 1, further comprising a first region connected to the high-penetrability region and configured to collect fluid from a wearer.

8. The wearable device of claim 7, wherein the encapsulant includes a first trench disposed at the first region.

9. The wearable device of claim 7, further comprising a second region connected to the high-penetrability region and configured to drain the fluid to external environment, wherein the second region is farther away from the wearer when the wearable device is worn by the wearer.

10. The wearable device of claim 9, further comprising a carrier disposed on the encapsulant, wherein the carrier includes a second trench disposed at the second region.

11. A wearable device, comprising:
    a transferring region configured to transfer matter from a body to the external environment; and
    a wiring region including a wiring element physically separated from the transferring region,
    wherein the transferring region comprises a first region and a second region at different sides of the wearable device, and the first region is closer to the body compared with the second region, and
    wherein the second region is configured to drain the matter.

12. The wearable device of claim 11, wherein the matter includes liquid or gas.

13. The wearable device of claim 12, wherein the matter includes sweat of the body.

14. The wearable device of claim 12, wherein the first region is configured to collect the matter from the body.

15. The wearable device of claim 12, wherein the transferring region further comprises a third region connecting the first region with the second region and configured to transfer the matter from the first region to the second region.

16. The wearable device of claim 15, wherein the wiring region includes a dielectric layer covering the wiring element, and the third region penetrates the wiring element.

17. The wearable device of claim 16, further comprising an encapsulant, wherein the third region penetrates the encapsulant.

\* \* \* \* \*